(12) United States Patent
Possover

(10) Patent No.: US 8,639,342 B2
(45) Date of Patent: *Jan. 28, 2014

(54) LAPAROSCOPIC IMPLANTATION OF NEUROSTIMULATORS

(71) Applicant: Marc Possover, Cologne (FR)

(72) Inventor: Marc Possover, Cologne (FR)

(*) Notice: Subject to any disclaimer, the term of this patent is extended or adjusted under 35 U.S.C. 154(b) by 0 days.

This patent is subject to a terminal disclaimer.

(21) Appl. No.: 13/621,375

(22) Filed: Sep. 17, 2012

(65) Prior Publication Data

US 2013/0023949 A1    Jan. 24, 2013

Related U.S. Application Data

(60) Division of application No. 12/626,274, filed on Nov. 25, 2009, now Pat. No. 8,489,191, and a continuation-in-part of application No. 11/708,209, filed on Feb. 20, 2007, now Pat. No. 8,019,423.

(60) Provisional application No. 60/774,758, filed on Feb. 17, 2006.

(51) Int. Cl.
*A61N 1/36* (2006.01)

(52) U.S. Cl.
USPC ........ 607/41; 607/1; 607/2; 607/40; 607/115; 607/116; 607/117; 607/118

(58) Field of Classification Search
USPC ............................. 607/1–2, 40–41, 115–118
See application file for complete search history.

*Primary Examiner* — Deborah Malamud
(74) *Attorney, Agent, or Firm* — Bachman & LaPointe, P.C.

(57) ABSTRACT

A method for altering operation of a nerve related to a given body condition includes the steps of identifying at least one nerve root of a nerve related to the given body condition; laparoscopically implanting at least one electrode on the nerve root; and operating the electrode to electrostimulate the nerve root and alter operation of the nerve.

10 Claims, 5 Drawing Sheets

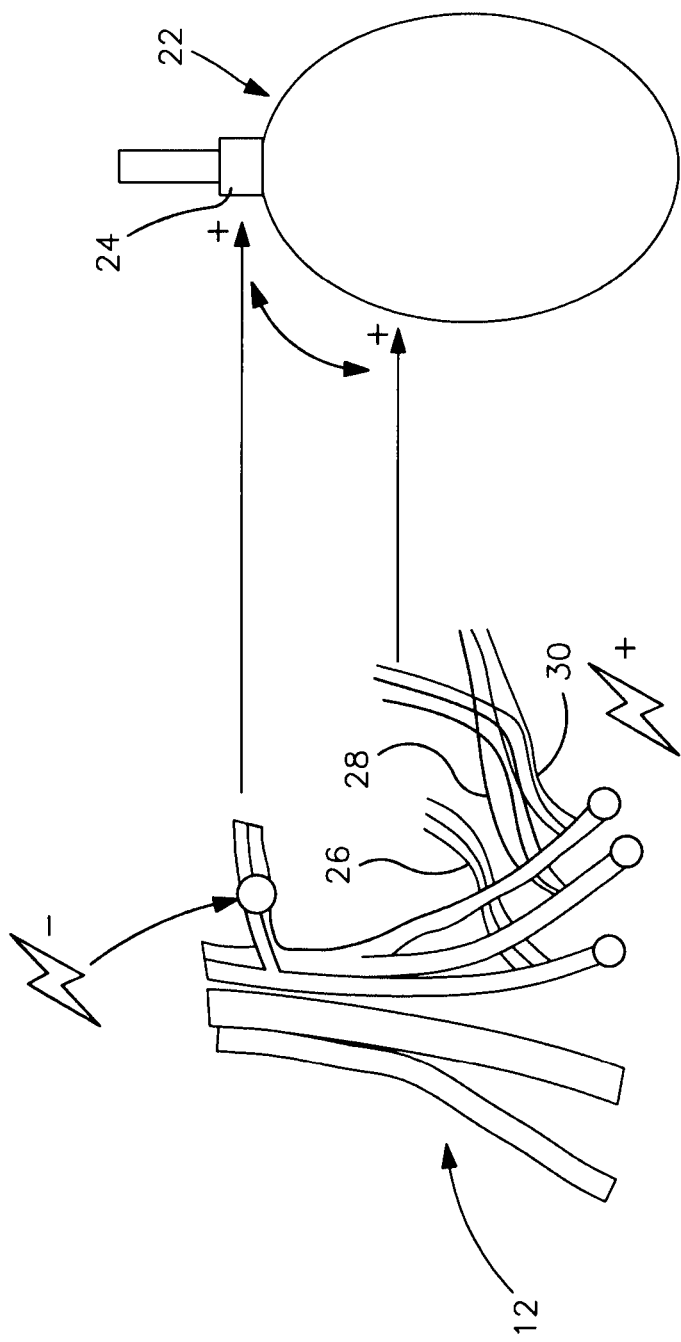

LAPAROSCOPIC IMPLANTATION OF NEUROSTIMULATORS

CROSS-REFERENCE TO RELATED APPLICATIONS

This application is a continuation-in-part of U.S. application Ser. No. 11/708,209 filed on Feb. 20, 2007, which claims the benefit of commonly owned provisional patent application No. 60/774,758 filed Feb. 17, 2006.

BACKGROUND OF THE INVENTION

The invention relates to stimulation of nerves to enhance and/or restore various body functions and/or to reduce pain.

Traumatic destruction or disease of the upper motoneurones inevitably leads to loss of motoric function such as standing up/walking, prehension or urination (voiding of the bladder) or defecation (bowel movement), and also to sensitive disorders such as pain or sensation loss. These conditions are serious and potentially life threatening, and great effort has been expended aimed at restoration of complete autonomy to individuals afflicted with such conditions.

Various types of neuroprothesis have been developed as a result, including muscular electrodes, neural electrodes and epidermal electrodes. The method of deployment of such electrodes has been problematic. One approach is transdermal, but this results in the need for large amounts of energy, as well as very precise placement and the inconvenience of always being connected to wires.

Implantation of the electrodes is far preferable, but this poses a new set of issues, including the need for implanting the energy source for the electrode as well as the method for implanting and new problems created by the implantation.

Based upon the foregoing, it is clear that the need exists for an improved method of stimulating nerves to enhance and/or restore various body functions.

It is the primary object of the invention to provide such a method.

It is a further object of the invention to provide this method in a manner which is safe and effective for the patient.

Other objects and advantages of the invention will appear below.

SUMMARY OF THE INVENTION

According to the invention, the foregoing objects and advantages have been attained.

According to the invention, a method is provided for altering operation of a nerve related to a given body condition, comprising the steps of: identifying at least one nerve root related to the given body condition; laparoscopically implanting at least one electrode at the nerve root; and operating the electrode to electrostimulate the nerve root and alter operation of the nerve.

This method can be used according to the invention to produce bladder function in a neurogenic bladder, to restore leg movement and the ability to stand up and walk, and to reduce pain. Other uses also fall within the broad scope of the present invention.

According to the invention, specific nerves and nerve strands can be identified and acted upon by laparoscopically implanted electrodes to provide the desired function. This provides for safe access to the proper nerves, especially in the pelvic region, and allows for implantation of electrodes, with their power sources if necessary, in a location which is convenient, reliable and safe to the patient.

BRIEF DESCRIPTION OF THE DRAWINGS

A detailed description of preferred embodiments of the invention follows, with reference to the attached drawings, wherein:

FIG. 6 illustrates still another option for stimulating nerves of the bladder.

DETAILED DESCRIPTION

The invention relates to laparoscopic implantation of neuroelectrodes on laparoscopically identified nerves and/or nerve strands to allow stimulation of those nerves and/or modulation of signals carried by those nerves. Laparoscopic procedures are particularly effective at identifying nerves in the pelvic area and implanting electrodes at nerves in that area, and the present invention is useful, for example, for restoring normal bladder function, restoring function of the muscle groups which allow a person to stand and the like. In addition, laparoscopic implantation of electrodes can be used to modulate signals through or from certain nerves to mediate or block pain.

Preferred embodiments of the invention are discussed below in connection with restoration of bladder function, restoration of function of the gluteal muscle group, restoration of sexual function, restoration of rectal function, spasticity of the lower extremities, modulation of pain signals, and concurrent nerve stimulation.

In connection with one aspect of the invention, laparoscopically implanted electrodes are used to restore normal bladder function to a patient who has lost this function, a condition which is referred to herein as a neurogenic bladder. Normal function of the bladder involves contraction of the bladder muscle during voiding, and relaxation of the bladder muscle at other times. Further, the bladder sphincter normally relaxes, or at least does not contract, during voiding, and contracts at other times. These functions are controlled by the central nervous system, and conditions affecting the nervous system can interfere with proper bladder function. For example functional disorders occur in paraplegia patients who normally have a hyperactive bladder. The bladder in these cases is overactive during filling, and during voiding or urination, both the sphincter muscle and the bladder contract simultaneously. This creates a dangerous condition wherein excessive pressure creates risk of damage to the kidneys.

Figure 2:
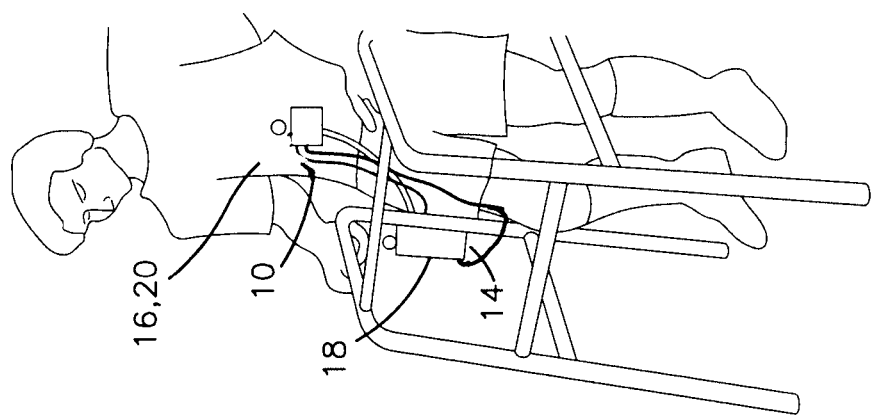
FIG. 2 schematically illustrates a system according to the invention in another area of use.
Figure 1:
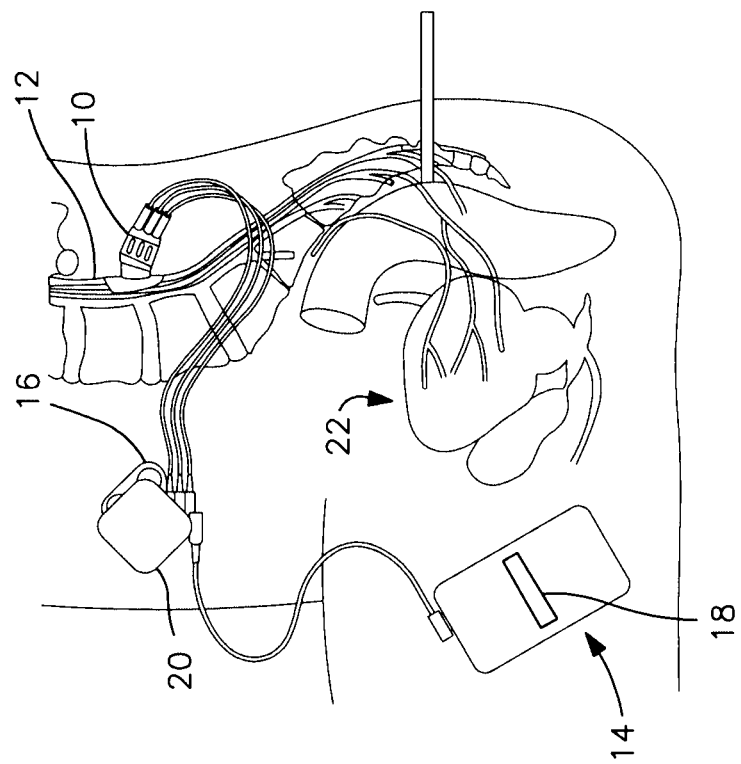
FIG. 1 schematically illustrates components of a system according to the invention in one area of use.

According to the invention, electrodes are implanted at specific roots of the sacral nerve and/or pudendal nerve and are operated to produce desired bladder function. FIG. 1 schematically illustrates a system according to the invention implanted in a human abdomen for controlling bladder function. According to the invention, electrodes 10 are implanted in communication with specific roots of the sacral nerve 12. An external power source 14 is provided in this embodiment and communicated with electrode 10 through a receiver 16, which is also implanted in the patient for receiving signals to operate electrodes 10. A controller 18 can be used to issue control signals and power signals through a transmitter 20 to communicate with receiver 16 and thereby operate electrode 10 as desired. It should be appreciated that the configuration as shown in FIG. 1 advantageously positions the electrode and related wiring and receiver within the pelvic area, which avoids problems associated with other configurations as described above. Similar to the FIG. 1 orientation for the sacral nerve, bladder function may also be controlled through the implantation of electrodes in the pelvic region in communication with roots of the pudendal nerve. It should be appreciated that external power source 14 could be a battery or any other readily available external source of power, and especially a source of a power signal which can be sent to an internal receiver, for example using radio frequency signals.

It has been found that the bladder and bladder sphincter muscles are controlled by nerves which run through the sacral spinal nerve and/or the pudendal pelvic region nerve. Further, current laparoscopic technology allows the sacral nerve to be differentiated to identify different sacral roots, referred to as S1-S5. If there is any doubt as to identification of the sacral roots and/or pudendal roots, electrostimulation can be used to confirm identification. This identification is used in the present invention to allow stimulation of specific sacral roots and/or pudendal roots to restore or otherwise influence certain functions of the body.

Figure 3:
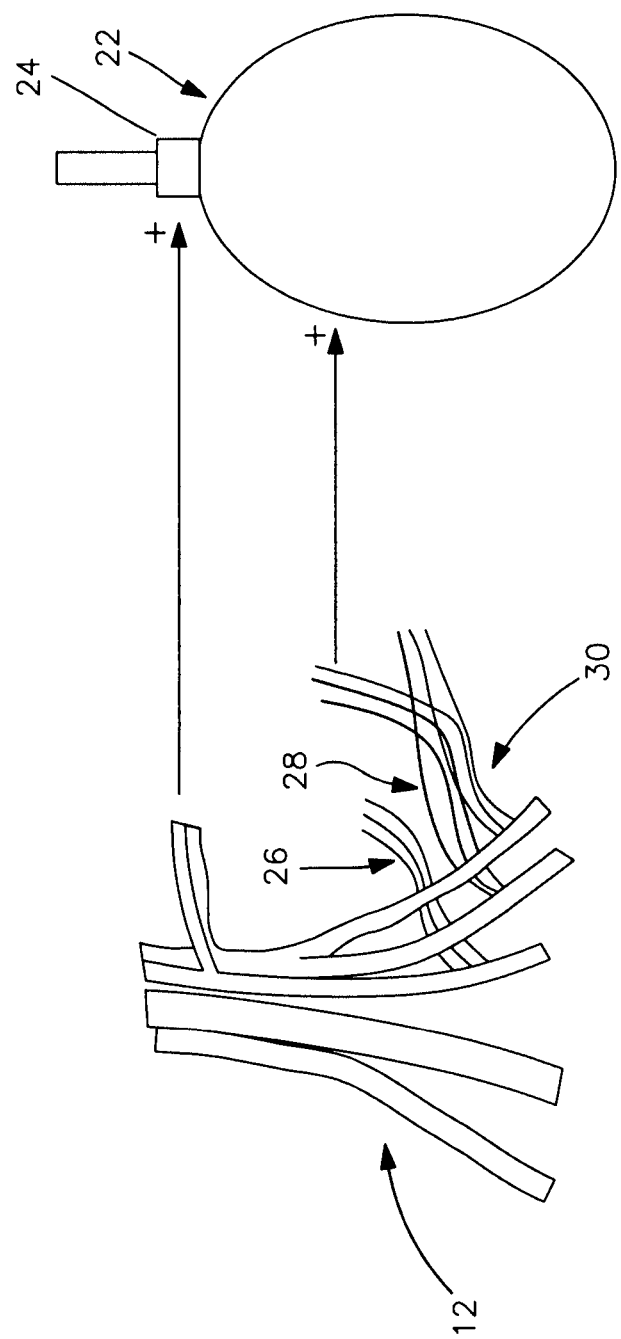
FIG. 3 illustrates normal pelvic innervation as it relates to the bladder.

FIG. 3 schematically illustrates a bladder 22, sphincter 24 and sacral nerve 12. All different sacral nerve roots also contain fibers for bladder contraction and for contraction of the sphincter of the bladder. The main fibers for the sphincter have been found in the sacral nerve root S2, while the main fibers for bladder and rectum contraction are found in the sacral nerve roots S3, S4 and S5. The aim is to produce an isolated contraction of the bladder without concomitant contraction of the sphincter. This is not feasible when electricity is applied on the entire sacral nerve roots together. According to the invention, three different options are provided for producing an elective contraction of bladder 22 without simultaneous contraction of sphincter 24 during electrostimulation.

Figure 4:
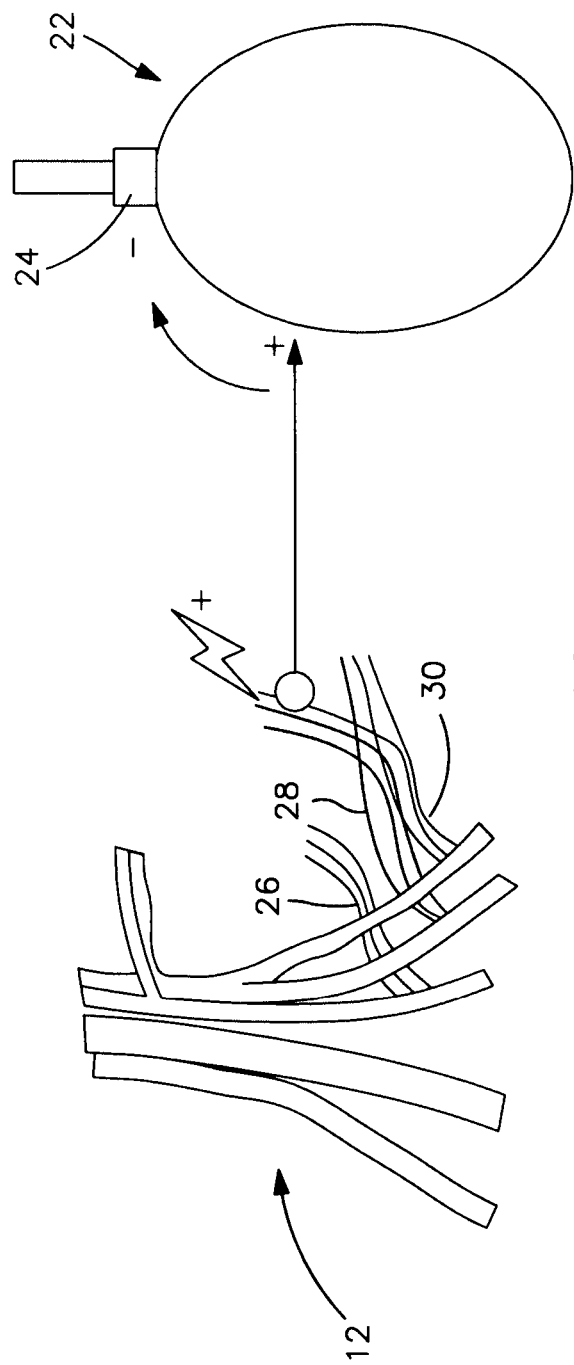
FIG. 4 illustrates one option for stimulating nerves of the bladder.

FIG. 4 illustrates one option in accordance with the invention, specifically, the elective stimulation of the pelvic parasympathetic nerves of the bladder and the rectum. FIG. 4 shows sacral nerve 12 separated into its different roots S1, S2, S3 and S4/5. In this approach, electrodes (schematically illustrated by wires 26, 28, 30) are attached to S2, S3 and S4/5. In order to selectively contract the bladder in this embodiment, selective stimulation can be directed to S3 and S4/5 to cause contraction of the bladder as desired. When it is no longer desired to have the contraction of the bladder, stimulation of S3 and S4/5 can be stopped during the filling phase of the bladder. During voiding of the bladder, the selective stimulation of S3 and S4/5 allows contraction of the bladder without contraction of the sphincter (which is mainly controlled through S2). Stimulation of the pudendal and/or sacral nerve allows for the effective control of bladder/rectum incontinence or overactivity.

Figure 5:
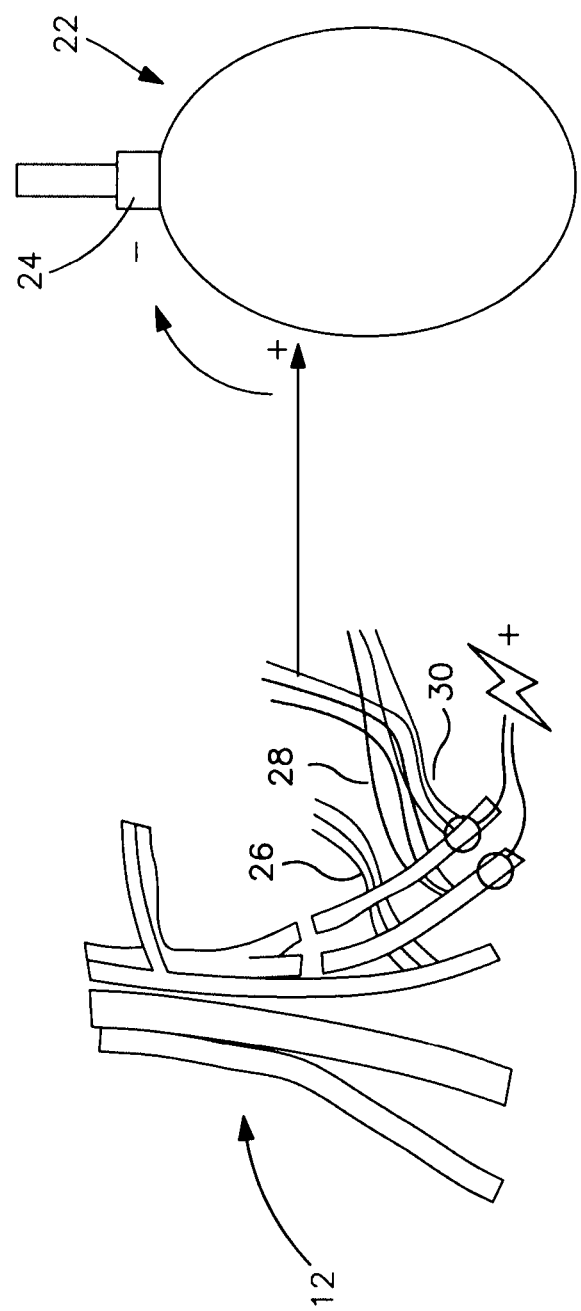
FIG. 5 illustrates another option for stimulating nerves of the bladder.

FIG. 5 illustrates a second option, similar to that illustrated in FIG. 4, but wherein sacral nerve roots S3 and S4/5 are cut distally after emergence of the parasympathetic nerves which permit an elective stimulation of the detrusor by stimulation of the sacral nerve roots S3 and S4/5. This approach allows such stimulation without concomitant stimulation of the pudendal nerve, thus without contractions of the sphincter nor muscles of the lower limbs. Since the sacral nerve root S2, which contains the major fibers for the sphincter, is kept intact under this approach, elective stimulation of S3 and S4/5 without stimulation of S2 produces electrical induced micturition, without incontinence during the filling phase of the bladder. Further, since S3 and S4/5 are not critical in connection with the functions of standing up and locomotion, no substantial side effects occur due to the distal transaction or cutting of the S3 and S4/5 sacral roots. Thus, option 2 advantageously allows for the same elective stimulation of the parasympathetic nerves as set forth in the approach of FIG. 4, but has the further advantage of avoiding unwanted contraction of the sphincter and/or muscles of the lower limbs during electrically induced micturition.

Turning to FIG. 6, a third option is provided and illustrated in accordance with the present invention. In this option, stimulation of nerve roots S3 and S4/5 can be implemented when desired for micturition, along with a simultaneous stimulation of a blocking signal of the pudendal nerve. By blocking signals through the pudendal nerve, the same result of the option illustrated in FIG. 5 can be accomplished, without the need for cutting the sacral nerve roots. In addition in a similar manner as described above for the sacral nerve, the bladder and rectum may be controlled through stimulation of the pudendal nerve.

As will be discussed further below, it is an aspect of the invention to use electrodes to issue a modulating signal to certain nerve roots. In this embodiment, an electrode can be used to modulate or neutralize signals carried by the pudendal nerve and, thereby, accomplish the same result as is accomplished in the embodiment of FIG. 4, but without having to cut S3 and S4/5.

It should of course be appreciated that in each of the above-described approaches, electrodes communicated directly with specific sacral nerve roots and/or pudendal nerve roots are used advantageously to electrically induce the proper conditions for micturition, specifically, an elective contraction of the bladder without simultaneous contraction of the sphincter.

Thus, according to the invention, laparoscopic differentiation of the sacral nerve roots S2, S3, S4/5, and/or pudendal nerve roots along with elective implantation of electrodes on each sacral nerve root and/or pudendal nerve root, and further with optional selective distal transection of the sacral nerve root and/or pudendal nerve root containing parasympathetic fibers for the detrusor or bladder muscle wall and for the rectum, allows different kinds of bladder voiding to be obtained. Specifically, this includes a per-stimulus micturition by elective isolated stimulation of the pudendal nerve roots and/or sacral nerve roots S3 and S4/5 on both sides of the body.

In situations where a per-stimulus micturition is unable to completely void the bladder, a concomitant stimulation of all sacral nerve roots S2-S4/5 could be able to produce a post-stimulus micturition as in the classic Brindley bladder, or isolated stimulation of S2 could be enough for opening the sphincter followed by a continuous stimulation of S3 and S4/5 for full emptying of the bladder by a continuous stream.

Stimulation according to the invention may be neurogenic or non-neurogenic. For example, any cell of the body may be stimulated. Bladder stimulation may also be myogenic. The stimulation of the bladder cells could also be used to control the bladder. Bladder cell stimulation to control myogenic bladder muscle tone, i.e. hypo-/atonia, is also readily accomplished according to this invention.

Laparoscopic implantation of an electrode for neuromodulation (quadripolar electrode) on the pudendal nerve root and/or sacral nerve roots S2 to S4/5 could be an alternative to the "surgical deafferentation" discussed above which induces sexual troubles, such as the loss of ejaculation, ejaculation precox and loss of erection in paralyzed patients. Pudendal nerve root and/or sacral nerve root stimulation could also be an alternative to sexual troubles in woman, such as anorgasmy, i.e. inability to orgasm. For example, a single multi-pole electrode can be attached functionally separately to each of S2-S4/5 of the sacral nerve and optionally also to S1. This electrode can be used to modulate any combination of S2-S4/5 which is necessary in order to prevent contraction of the bladder during filling. During voiding or micturition, specific poles of the electrode can be operated to induce the desired actions of the bladder and sphincter as described herein.

The electrodes, after implanting, must be powered and also controlled to emit the desired signal or stimulus to the nerve. According to the invention, the power source for the electrode can be external, or can be implanted along with the electrode, preferably as a single structure.

If the application of the device concerns neuromodulation (e.g. pain therapy), only low voltages are necessary for the electrode, and low energy consumption occurs. Typical parameters include 8-10 Volts, about 25 Hz, and 250 microsecond pulses. For such an application, a battery (e.g. pacemaker battery, type Itrel 3, supplier Medtronic) is implanted along with the electrodes.

In the case of re-establishment of body functions, e.g. motions of paralyzed patients, higher voltages (20-30V, 30 Hz) are required which would be problematic for implanted batteries. Here, electrical energy is transmitted from the external via radio frequency signals, for example from transmitter 20 to receiver 16. Further, in this embodiment, a battery would not be necessary since the stimulation would not be permanent—as in the case of pain therapy—but instead energy is applied only when needed, e.g. for emptying the bladder.

A receiver is also provided, and preferably implanted in the patient to receive control signals which can be generated by the patient or caregiver, for example using some form of control unit. The receiver is operatively communicated with the electrodes to provide signals to the electrodes as desired.

According to the invention, wiring between the electrodes and/or power source or receiver can be safely passed through the pelvic region, also using laparoscopic techniques, which are much more user friendly than other surgically installed electrodes and/or wiring.

According to another aspect of the invention, laparoscopic implantation of electrodes can be used to restore pelvic or leg functions. In one aspect of the invention, electrodes are implanted to restore the functions of standing up and walking. Before a paralyzed patient can walk, he must be able to stand up and remain standing. The most important muscle activity is the contraction of the buttock muscle. In order to stimulate such muscles, placement of electrodes in a friction, pressure or sitting area must be avoided. Incisions in the buttock region are also unacceptable.

Placement of electrodes laparoscopically according to the invention, on the muscle nerves themselves, leads to a homogenous contraction of the whole muscle as desired. The location of the electrodes should not be affected by movement, pressure or friction, and the location must be such that all muscles required for a particular motion are included.

Stimulation of the gluteal musculature is necessary for the patient to be able to stand up and this presents the main problem. Operative access for placement of the electrodes on the Nervus gluteus superior and inferior is required. This is an extremely short nerve, and it divides directly at the opening of the foramen ischiadicus magnus into numerous branches. According to the invention, suitable electrodes are placed directly on the development point of these nerves out of the plexus sacralis, in the pelvis. Transperitoneal placement of electrodes through laparoscopy enables optimal placement of the electrodes in the pelvis where all the stimulation possibilities necessary for standing up and walking can be recorded and/or produced with only a small amount of effort. For paralyzed patients, anesthetic is not generally even needed since the lower extremity regions are no longer sensitive.

Electrodes for controlling the gluteal musculature are preferably placed on one or more of the nerves discussed below. An intrafascicular neurolysis is performed on the Nervus femoral, which is a nerve with mixed functions, as only the motoric fibers should be stimulated. The motoric fascicule is differentiated from the sensitive fasciculation with the aid of neurostimulation. The nerves identified for treatment with electrodes include the Nervi Glutei inferior and superior, the musculus iliopsoas nerve, and the plantar flexion nerve.

An interfasciculator neurolysis is also performed and the fibers of the Nervus peroneus are isolated with the aid of neurostimulation. Placement of electrodes is performed on both sides of the body.

Sciatic stimulation of the lower extremities for the control of spasticity disorders, such as muscular sclerosis, polyneuropathie, tetraplegics, paraplegics and the like, is also readily accomplished according to the invention.

As with the embodiment dealing with bladder function discussed above, electrodes used in the motor function aspects and sciatic stimulation of the invention are preferably implanted, and powered with a suitable, preferably external, power source for same, and also along with a receiver for receiving commands for the electrodes, and any wiring needed to communicate these elements.

Turning to another aspect of the invention, neuromodulation for pain therapy is also readily accomplished according to the invention.

Neuromodulation is based upon the fact that pain information is transported through one or several nerves to the brain. The analgesic aims at blocking the information flow on the way between the point of pain and the brain. Neuromodulation cannot block this pain information, but modulation of the information can neutralize the signal and prevent the patient from centrally receiving the pain information.

Of course, the method of the present invention requires that the electrode be placed between the stimulus which produces the pain information and the central nervous system. All nerves which transmit the pain information must be included in the neuromodulation in order for the method to have the desired effect.

As set forth above, pelvic nerves can now be reached by laparoscopy. Since all nerves of the lower extremities and the pelvis must reach the sacral spinal cord, the numerous leg nerves in the pelvis concentrate eventually only on the nervus obturatorius, the nervus femoralis, genitofemoralis, ilio-inguinalis, the nervus ischiadicus, the plexus sacralis and the Nervus pudendus. Laparoscopic implantation of electrodes can reach each of these nerves, including some which lie deep within the pelvis, well hidden behind vessels, and in locations which are unreachable through other techniques. Placement of a single electrode on the nervus femoralis and a further one on the nervus ischiadicus, for example, includes all "pain nerves" which are relevant in therapy for phantom pain after amputation. Placement of electrodes on the sensitive nerves in the pelvis (Plexus hypogastricus inferior, nervi hypogastrici inferiors, Trunci sympathici, Nervus ilio-inguinale, Nervus genitofemoralis, and the like) can also serve to fight lower abdominal pain.

Also as set forth above, the power source for implanted electrodes for neuromodulation according to the invention is preferably also an implanted device, and the electrode and power source can advantageously be implanted together.

It will be appreciated that the process of the present invention can be used in all situations of pelvic pain, pelvic neuralgias and/or pelvic dysfunctions. These include phantom pain after amputation or other trauma to the lower limbs, polyneuropathy of the lower limbs due to diabetic, idiopathic, alcoholic, auto immune, post-chemotherapy and other conditions, pudendal neuralgia/Alcock's canal syndrome, sciatalgia, neuralgia of the branches of the sciatic nerve, neuralgia of the ilio-inguinal nerve/ilio-hypogastric nerve/genital femoral nerve, neuralgia of the femoral nerve, central or lateral pelvic pain syndrome, secondary to pelvic surgery (neuromodulation of the hypogastric plexus superior and/or inferior), interstitial cystitis, neurologic impotence/anejaculation, bladder hyperactivity with pain from multiple sclerosis/multi focal encephalopathy, bladder/rectum incontinence, spina bifida, myelomeningocele and numerous others.

Two examples are outlined below which illustrate fibroscopic implantation of neural prostheses on pelvic nerves in accordance with the present invention. These procedures were carried out to perform neuromodulation of pelveo-abdominal nerves.

In situations of pelvic pain/neuralgia, after surgical treatments, symptomatic medical treatments are widely indicated and neuro-electrotherapy is also an option. Actual electrotherapy is based upon the direct neuromodulation of the nerves by an implantable device at the level of the spinal cord, the sacral nerve or directly on the peripheral nerves of the lower limb. However, even when considerable development in the electrodes and implantation techniques was accomplished, the indication of the effect of neuromodulation on the pelvic nerves remained limited. In all reported techniques, the implantation of the electrode is done mostly by blunt percutaneous and puncture and implantation in deep placed nerves such as the sciatic nerve or the pudendal nerve in their endopelvic pathways. Since most conventional devices are built with just one or two channels, peripheral neuromodulation should involve at least two nerves at the same time, but never more than is required for the desired procedure.

A laparoscopic procedure was used to approach the pelvic nerves for implantation of electrodes on their endopelvic pathways. Because quadropolar electrodes are authorized for peripheral nerve neuromodulation and pain situation and are easy to use by laparoscopy, the procedure of the present invention in connection with the sciatic nerve, the pudendal nerve, all sacral nerve roots before or after emergence of the pelvic splanchnic nerves or on pelvio-abdominal nerves as the genital femoral, ilio-inguinal and ilio-hypogastric nerves, or the hypogastric plexus also becomes feasible.

Testing was started with this field of patients after failure of all other classical techniques of pain management, including failure or contraindications for classical technique of nerve stimulation.

The first implantation was done in a 58 year old female for treatment of neuralgia of the genitofemoral and ilio-inguinal nerves secondary to a previous herniorraphy and for treatment of a unilateral pudendal neuralgia secondary to a radical hysterectomy and pelvic irradiation for endometrial carcinoma. One electrode was placed on the genitofemoral, the ilio-inguinal and the hypoinguinal nerves together and a second electrode was placed on the sacral nerve roots S2, S3 and S4/5.

The second implantation was performed on the endopelvic portion of a sciatic nerve in a 72 year old male for treatment of refractory phantom pain and neuralgia of the posterior cutaneous nerve after leg amputation. Neuromodulation induced in both patients a permanent reduction in pain without need of any further medical treatment.

Requests from patients in situations where classic pain therapies have failed or been accompanied by unacceptable side effects have led to further indications for this procedure. The sacral nerve roots procedure of the present invention produced unexpected excellent results for treatment of diabetic polyneuropathy of the lower extremities, refractory interstitial cystitis and pelvic pain/neuralgia secondary to rectum resection, radical prostatectomy or radical hysterectomy. According to the invention, neuromodulation of the sacral nerve roots is used to cure concomitantly pelvic/lower limb neuralgias and bladder/rectum dysfunctions in patients with multiple sclerosis or spina bifida. The subject matter of the present application was also introduced to the field of functional electrical stimulation, or FES, for recovery of functions in paralyzed patients.

On Apr. 27, 2006, a Finetech-Brindley bladder controller was implanted on the endopelvic sacral roots in a Th8 completely paralyzed female who had previously undergone the removal of a Brindley controller due to an arachnoiditis after an extrathecal implantation with an intradural sacral deafferentation. Because no laminectomy is required for implantation of the electrodes, the present procedure does not expose the patient to a risk of arachnoiditis or of spinal liquid leakage. Thus, electrostimulation permits a post stimulant emptying of the bladder for the patient, as in the classic Brindley technique. Delivery of the patient occurred on the fourth postoperative day.

It should be appreciated that, according to the invention, electrodes are advantageously implanted into patients suffering from a neurogenous bladder, paralysis, spasticity, sexual dysfunctions, pain and the like, in order to at least partially restore a normal function of the afflicted area. It is also to be appreciated that intermittent or continuous stimulation and implantation of specific pundendal nerve roots and/or sciatic nerve roots is substantially similar to the implantation and stimulation of the specific sacral nerve roots identified in this disclosure. As with specific sacral nerve roots, electrostimulation of specific pundendal nerve roots and or sciatic nerve roots is used to identify the specific root for the desired function. The electrodes could also be implanted in order to facilitate concurrent stimulation of differing nerves for differing pathologies and afflictions. All implantations are done in a manner, which avoids radical surgery and its inherent risks.

It should also be appreciated that the present detailed description of the invention is given in terms of preferred embodiments of the invention, and that various modification of steps, parts and the like would be readily apparent to a person of skill in the art, and that such modifications are considered to fall within the broad scope of the present invention.

We claim:

1. A method for altering operation of a nerve related to a given body condition, comprising the steps of:
    laparoscopically entering the body through the abdomen;
    laparoscopically identifying at least one nerve root of an endopelvic portion of a nerve related to the given body condition, wherein the given body condition is a non-neurogenic condition;
    laparoscopically implanting at least one electrode on the endopelvic portion of the nerve root; and
    operating the electrode to electrostimulate the nerve root and alter operation of the nerve.

2. The method of claim 1, wherein the implanting step further comprises implanting a receiver for the electrode, and wherein the operating step comprises sending a signal to the electrode through the receiver.

3. The method of claim 2, wherein the sending step further comprises sending a power signal to the receiver whereby the electrode is powered from an external source.

4. The method of claim 1, wherein the implanting step comprises implanting an electrode to stimulate a first group of bladder cells which control bladder sphincter and a second group of bladder cells which control bladder musculature, whereby elective contraction of the bladder is possible without a simultaneous contraction of the bladder sphincter.

5. The method of claim 4, wherein electrostimulation is used to identify the first group of bladder cells and the second group of bladder cells.

6. The method of claim 1, wherein the given body condition comprises spasticity of the lower extremities, and wherein the implanting step comprises implanting the electrode to stimulate sciatic nerve roots.

7. The method of claim 6, wherein electrostimulation is used to identify the sciatic nerve root associated with the spasticity of the lower extremity.

8. The method of claim 1, wherein the given body condition comprises a sexual dysfunction, and wherein the implanting step comprises implanting the electrode at the nerve root selected from the group consisting of pudendal nerve root, sacral nerve root and combinations thereof.

9. The method of claim 1, wherein the implanting step comprises implanting a plurality of electrodes at a location selected from the group consisting of a plurality of nerve roots and groups of body cells, which are related to a plurality of given body conditions, wherein the nerve root is selected from the group consisting of pudendal nerve root, sacral nerve root, sciatic nerve root and combinations thereof.

10. The method of claim 9, wherein electrostimulation is used to identify the nerve roots or groups of body cells.

\* \* \* \* \*